(12) United States Patent
Wolf

(10) Patent No.: US 9,018,405 B2
(45) Date of Patent: Apr. 28, 2015

(54) CERAMIDE DIMERS AND USE THEREOF AS PHARMACEUTICAL PREPARATION OR COSMETIC PREPARATION

(76) Inventor: Hans-Uwe Wolf, Neu-Ulm (DE)

( * ) Notice: Subject to any disclaimer, the term of this patent is extended or adjusted under 35 U.S.C. 154(b) by 486 days.

(21) Appl. No.: 13/380,789

(22) PCT Filed: Jun. 23, 2010

(86) PCT No.: PCT/EP2010/003875
§ 371 (c)(1),
(2), (4) Date: Feb. 14, 2012

(87) PCT Pub. No.: WO2010/149383
PCT Pub. Date: Dec. 29, 2010

(65) Prior Publication Data
US 2012/0129933 A1 May 24, 2012

(30) Foreign Application Priority Data
Jun. 23, 2009 (EP) .................................... 09008218

(51) Int. Cl.
C07C 233/09 (2006.01)
C07C 235/08 (2006.01)
C07C 233/16 (2006.01)
C07C 233/18 (2006.01)
C07C 233/34 (2006.01)
C07C 233/20 (2006.01)
A61Q 19/00 (2006.01)

(52) U.S. Cl.
CPC ............... *C07C 235/08* (2013.01); *A61Q 19/00* (2013.01); *C07C 233/16* (2013.01); *C07C 233/18* (2013.01); *C07C 233/34* (2013.01); *C07C 233/20* (2013.01)

(58) Field of Classification Search
None
See application file for complete search history.

(56) References Cited

U.S. PATENT DOCUMENTS

| | | | |
|---|---|---|---|
| 5,753,093 A | 5/1998 | Raguse et al. | |
| 5,820,873 A * | 10/1998 | Choi et al. | ................. 424/283.1 |
| 6,358,919 B1 | 3/2002 | Kanie et al. | |
| 7,553,981 B2 * | 6/2009 | Wolf et al. | ...................... 554/78 |
| 7,964,640 B2 | 6/2011 | Wolf | |
| 2006/0258616 A1 | 11/2006 | Wolf et al. | |
| 2009/0012166 A1 | 1/2009 | Wolf | |

(Continued)

FOREIGN PATENT DOCUMENTS

| | | |
|---|---|---|
| DE | 198 41 794 A1 | 3/2000 |
| EP | 1 201 736 A1 | 5/2002 |
| JP | 2002-047261 A | 2/2002 |

(Continued)

OTHER PUBLICATIONS

KAO Corp., External Preparation Composition, 2002, JP 2002-047261, English Translation, 12 pages.*

(Continued)

*Primary Examiner* — Yate K Cutliff
(74) *Attorney, Agent, or Firm* — Leydig, Voit & Mayer, Ltd.

(57) ABSTRACT

The invention relates to ceramide dimers which are constructed from two ceramide molecules which are crosslinked to each other via their lipophilic end. The ceramide molecules thereby have at least one hydrophilic group at their hydrophilic end for increasing the hydration shell of the dimer. The ceramide dimers according to the invention can be used as pharmaceutical preparation or as cosmetic preparation.

8 Claims, 3 Drawing Sheets

HO-Ceramide-CH₃    CH₃ Fatty Acid-OH
HO-Fatty Acid-CH₃    CH₃-Cholesterol-OH
Serine-O-Ceramide-CH₂-O-CH₂-Ceramide-O-Serine
HO-Ceramide-CH₃    CH₃-Ceramide-OH
HO-Ceramide-CH₃    CH₃-Fatty Acid-OH
Serine-O-Ceramide-CH₂-O-CH₂-Ceramide-O-Serine
HO-Ceramide-CH₃    CH₃-Cholesterol-OH
HO-Fatty Acid-CH₃    CH₃-Cermide-OH
Serine-O-Ceramide-CH₂-O-CH₂-Ceramide-O-Serine
HO-Cholesterol-CH₃    CH₃-Ceramide-OH
HO-Fatty Acid-CH₃    CH₃-Cholesterol-OH ↑        ↑
Membrane Surface    Membrane Surface

(56) References Cited

U.S. PATENT DOCUMENTS

2009/0105199 A1    4/2009    Wolf
2012/0329737 A1    12/2012    Wolf et al.

FOREIGN PATENT DOCUMENTS

| WO | WO 00/68238 A1 | 11/2000 |
| WO | WO 03/068255 A1 | 8/2003 |
| WO | WO 2004/108124 A1 | 12/2004 |
| WO | WO 2005/063688 A1 | 7/2005 |
| WO | WO 2007/006549 A2 | 1/2007 |
| WO | WO 2007/006550 A2 | 1/2007 |

OTHER PUBLICATIONS

Suzuki, H. et al., Synthesis of Ceramide Mimics with a pseudo cyclic framework, 2003, Synlett, No. 14, pp. 2163-2166.*

Coderch et al., "The Effect of Liposomes on Skin Barrier Structure," *Skin Pharmacology and Applied Skin Physiology*, vol. 12, No. 5, pp. 235-246 (1999).

"Fachärztliches, dermatologisches Gutachten über die Hydra Tationsbestimmung mit dem Corneometer: Ceramide Serin," Dermatest GmbH, 11 pgs, (Apr. 6, 2009).

"Fachärztliches, dermatologisches Gutachten über die Hydra Tationsbestimmung mit dem Corneometer: Ceramide Dimer," Dermatest GmbH, 11 pgs, (Apr. 6, 2009).

Fachärztliches, dermatologisches Gutachten über einen Test zum Transepidermalen Wasserverlust (TEWL) An Der Menschlichen Haut: Ceramide Dimer, Dermatest GmbH, 11 pgs. (Apr. 6, 2009).

Fachärztliches, dermatologisches Gutachten über einen Test zum Transepidermalen Wasserverlust (TEWL) An Der Menschlichen Haut: Ceramide Serin, Dermatest GmbH, 11 pgs. (Apr. 6, 2009).

Mc Intosh et al., "X-ray diffraction analysis of isolated skin lipids: reconstitution of intercellular lipid domains," *Biochemistry*, vol. 35, No. 12, pp. 3649-3659 (1996).

Tanno et al., "Nicotinamide increases biosynthesis of ceramides as well as other stratum corneum lipids to improve the epidermal permeability barrier," *Br J. Dermatol*, vol. 143(3), pp. 524-531 (2000).

Velkova et al., "Influence of the lipid composition on the organization of skin lipid model mixtures: an infrared spectroscopy investigation," *Chem. Phys. Lipids*, vol. 117(1-2), pp. 63-74 (2002).

European Patent Office, International Preliminary Report on Patentability in International Patent Application No. PCT/EP2010/003875 (Jan. 12, 2012).

Arikawa et al., "Decreased Levels of Sphingosine, A Natural Atnimicrobial Agent, may be Associated with Vulnerability of the Stratum Corneum from Patients with Atopic Dermatitis to Colonization by *Staphylococcus aureus*," *J. Invest Dermatol*, vol. 119(2), pp. 433-439 (2002).

Coderch et al., "The Effect of Liposomes on Skin Barrier Structure," *Skin Pharmacology and Applied Skin Physiology*, vol. 12, No. 5, pp. 235-246 (1999) Abstract only.

Dijkstra et al, "Transmission of Binding Information across Lipid Bilayers", *Chemistry—A European Journal*, vol. 13, No. 25, pp. 7215-7222, (2007).

Félétou et al, "Vascular endothelial growth factor and the in vivo increase in plasma extravasation in the hamster cheek pouch", *British Journal of Pharmacology*, vol. 132, No. 6, pp. 1342-1348, (2001).

Fuss et al, "Carbohydrate-carbohydrate interaction prominence in 3D supramolecular self-assembly", *Journal of Physical Chemistry Part B: Condensed Matter, Materials, Surfaces, Interfaces & Biophysical*, vol. 112, No. 37, pp. 11595-11600 (2008).

Hsieh et al, "Structural Effects in Novel Steroidal Polyamine-DNA Binding", *Journal of the American Chemical Society*, vol. 116, No. 26, pp. 12077-12078 (1994).

Macheleidt et al., "Deficiency of Epidermal Protein-Bound ω-Hydroxyceramides in Atopic Dermatitis," *J. Invest Dermatol*, vol. 119(1), pp. 166-173 (2002).

Mao-Qiang et al., "Secretory Phospholipase $A_2$ Activity is Required for Permeability Barrier Homeostatis," *J. Invest Dermatol*, vol. 106(1), pp. 57-63 (1996).

Mao-Qiang et al.,"Optimization of Physiological Lipid Mixtures for Barrier Repair," *J. Invest Dermatol*, vol. 106(5), pp. 1096-1101 (1996).

Mao-Qianget al., "Fatty Acids Are Required for Epidermal Permeability Barrier Function," *J. Clin. Invest*, vol. 92, pp. 791-798 (1993).

Maue et al, "Bifunctional Bisamphiphilic Transmembrane Building Blocks for Artificial Signal Transduction", *Synthesis*, No. 14, pp. 2247-2256 (2008).

Mc Intosh et al., "X-ray diffraction analysis of isolated skin lipids: reconstitution of intercellular lipid domains," *Biochemistry*, vol. 35, No. 12, pp. 3649-3659 (1996) Abstract only.

Morzycki et al., "Synthesis of Dimeric Steriods as Components of Lipid Membranes," *Tetrahedron*, vol. 53, No. 30, pp. 10579-10590 (1997).

Pilgrim et al., "Aberrant Lipid Organization in Stratum Corneum of Patients with Atopic Dematitis and Lamellar Ichthyosis," *J. Invest Dermatol*, vol. 117(3), pp. 710-717 (2001).

Runquist et al, "Design, synthesis, and characterization of bis-phosphatidylcholine, a mechanistic probe of phosphatidylcholine transfer protein catalytic activity", *Biochimica et Biophysica Acta*, vol . 940, No. 1, pp. 10-20 (1988).

Tanno et al., "Nicotinamide increases biosynthesis of ceramides as well as other stratum corneum lipids to improve the epidermal permeability barrier," *Br J. Dermatol*, vol. 143(3), pp. 524-531 (2000) Abstract only.

Velkova et al., "Influence of the lipid composition on the organization of skin lipid model mixtures: an infrared spectroscopy investigation," *Chem. Phys. Lipids*, vol. 117(1-2), pp. 63-74 (2002. Abstract only.

European Patent Office, International Search Report in International Patent Application No. PCT/EP2010/003875 (Jan. 17, 2011).

European Patent Office, Written Opinion in International Patent Application No. PCT/EP2010/003875 (Jan. 17, 2011).

European Patent Office, International Search Report in International Patent Application No. PCT/EP2010/003876 (Mar. 28, 2011).

European Patent Office, Written Opinion in International Patent Application No. PCT/EP2010/003876 (Mar. 28, 2011).

Nicholas et al., "Enantiodivergent Biosynthesis of the Dimeric Sphingolipid Oceanapiside from the Marine Sponge Oceanapia phillipensis. Determination of Remote Stereochemistry," *J. Am. Chem. Soc.*, 122:17, 4011-4019 (2000).

\* cited by examiner

CERAMIDE DIMERS AND USE THEREOF AS PHARMACEUTICAL PREPARATION OR COSMETIC PREPARATION

This patent application is the U.S. national phase of International Application No. PCT/EP2010/003875, filed on Jun. 23, 2010, which claims the benefit of European Patent Application No. 09008218.1, filed Jun. 23, 2009, the disclosures of all of which are incorporated herein by reference in their entirety for all purposes.

The invention relates to ceramide dimers which are constructed from two ceramide molecules which are crosslinked to each other via their lipophilic end. The ceramide molecules thereby have at least one hydrophilic group at their hydrophilic end for increasing the hydration shell of the dimer. The ceramide dimers according to the invention can be used as pharmaceutical preparation or as cosmetic preparation.

Basically, all biological membranes, in particular cell membranes, comprise so-called lipids and lipid-analogous substances as essential components which are structurally constructed from a lipophilic (hydrophobic) and a hydrophilic (lipophobic) molecule part, so that they hence have a so-called amphiphilic structure which is in part very greatly pronounced.

The amphiphilic structure of the ceramides, i.e. the simultaneous presence of a (strongly) hydrophobic and of a hydrophilic, polar component of the molecular structure, leads to the ceramides in an aqueous phase (generally together with other lipids) arranging themselves spontaneously to form a lipid double layer, a so-called "lipid bilayer" which represents inter alia the basis of the structure of biological membranes. The constructional principle of this bilayer is the same for ceramides and all other lipids and lipid-analogous substances: they are arranged in two parallel layers which are situated closely together, respectively the hydrophobic radicals of the ceramides being situated directly opposite each other and coming into contact. Hence they form the hydrophobic inner region of the membrane bilayer, whilst the hydrophilic radicals are in contact on both sides of the lipid bilayer with the aqueous phase of the extra- and intracellular space. The tendency to form this ceramide bilayer resides both within and outside an organism, e.g. in an aqueous system in which the properties of the ceramide bilayers can be examined in experimental arrangements designed specially for this purpose.

In the case of all nine ceramides known to date and also in the case of the analogous hydroxyceramides, the lipophilic region consists of the alkane radical of the sphingosine basic structure and the fatty acid radical (acyl radical) coupled to the NH group of sphingosine, whilst the hydrophilic region is formed by the two OH groups and by the —NH—CO— structure of the sphingosine basic body.

The structure of the ceramide bilayer in an organism is formed spontaneously. Although it has significant stability, the possibility exists for example in the presence of a lipid metabolic disturbance that a biological membrane loses a part of its ceramide components because these components are formed either too slowly and/or in an inadequate amount or are metabolised too rapidly. As a result, the relevant membranes are depleted of the respective ceramide components, which leads inter alia to a disorder of the membrane structure and function.

The physiological composition of the membrane ceramides of the stratum corneum of human skin is however still of essential importance for the normal structure and function of the skin for a second reason. The presence of an adequate content of ceramides ensures the unrestricted capacity of the skin to bind a physiological quantity of water. The loss of a part of the stratum corneum ceramides therefore leads to a restriction in the water-binding capacity, which can be established clinically by so-called corneometry. Furthermore, in the course of the ceramide loss, the so-called transepidermal water loss (TEWL) of the skin is increased. This is revealed in the occurrence of a "dry" and wrinkled skin which occurs in particular frequently, but not exclusively, with increasing age.

A known example of such changes is the depletion of ceramides of the lipid bilayers of the stratum corneum of human skin. For example, in the case of atopic dermatitis, low contents inter alia of ceramide 3, ceramide 4, ω-hydroxy ceramides in the skin of patients (Macheleidt O, Kaiser H W and Sandhoff K (2002): J Invest Dermatol 119(1): 166-173) and sphingosine were revealed.

Skin changes and skin diseases as a result of the loss of lipids, in particular of ceramides, are for example:
atopic dermatitis
"dry" skin xerosis, xeroderma
dyshidrotic eczema
chronic cumulative toxic contact eczema
ageing skin
skin severely affected by UV light
sebostasis
keratinisation disorders
diabetes-caused skin damage In particular in the field of clinical medicine, it is desirable in the mentioned cases of diseases to change and/or to stabilise the structure of the biological membrane present in the organism, i.e. the lipid bilayers, in a suitable manner.

According to recent knowledge relating to the pathomechanism of atopic dermatitis (Arikawa J, Ishibashi M, Kawashima M, Takagi Y, Ichikawa Y, Imokawa G (2002): J Invest Dermatol 119(2): 433-439) and related diseases, the cause of the susceptibility of the skin in the case of such a disease is inter alia a changed lipid metabolism or reduced lipid content of the stratum corneum. These changes relate, in addition to the fatty acid metabolism, inter alia, also to the ceramide metabolism.

The current possibilities for alleviating the symptoms and consequences of the mentioned skin diseases, in particular atopic dermatitis (there is still no talk at present of a cure), are still very limited. Topical application of special glucocorticoids and immunosuppressive active substances is associated with significant risks because of the toxicity of these substances. Specific corticoids even cause an almost counterproductive effect by leading to a loss of lipids, in particular of ceramides, cholesterol and free fatty acids.

Taking into account the current state of knowledge about the importance of a physiological lipid composition of the stratum corneum membranes, it is logical to attempt to compensate for deficits in membrane lipids which exist in the stratum corneum by means of exogenous supply. Therefore in practice attempts have been made to supply the missing lipids, in particular ceramides, to the changed or diseased skin with the help of ointments, creams and the like. This is effected for example by lipid preparations which are specially formulated for this purpose, inter alia by using liposomes as a vehicle for transporting lipids into the skin. Numerous products with contents of ceramides are meanwhile on the market for cosmetic purposes and for the therapy of the mentioned skin diseases.

The therapeutic measures portrayed here should of course be regarded as correct in principle since they logically attempt to compensate for the deficits existing in the stratum corneum in ceramides. Experience gained with these therapeutic measures during the last few years reveals however that, despite the correctness in principle of the therapeutic approach, the results of these cosmetic and curative treatments are in no way convincing. In part, the success of the implemented measures is unreliable or not sustainable. Even if an approximately acceptable success in the curative treatment arises, a treatment of this type has at least two serious disadvantages:

The extent of the successful cure is not so great that it can be called complete recovery of the diseased skin.

In order to ensure to some extent an acceptable successful cure of the skin over a fairly long period of time, the ceramides must be supplied permanently to the skin at short time intervals, i.e. the active substances used do not show any sustained efficacy.

Both disadvantages can be attributed to a common cause. The ceramides are not static components of the skin, rather they are intermediate products of a reaction sequence in which the ceramides required by the skin are provided for example by synthesis processes of the organism or from nutrition and are incorporated in the biological membrane. After detection of their function as a membrane component of the stratum corneum, they are subsequently included in specific decomposition reactions of the organism.

This reaction sequence represents a steady state in which a specific quantity of ceramides is synthesised by the effect of specific enzymes and is released again after a corresponding dwell time in the membrane from the latter in order then to be eliminated via enzyme-controlled metabolic decomposition processes. Hence a certain throughput of substance is present. The ceramides supplied exogenously as skin therapeutic agents are included in this reaction sequence. If there is a priori a disruption in this reaction sequence which then leads to a pathologically reduced ceramide composition of the stratum corneum, then it is to be expected that the exogenous supply of ceramides in the form of a therapeutic agent can fundamentally change nothing or not much in this pathological state since the exogenously supplied ceramide component of the organism is metabolised in the same way as is the case with the ceramide component made available endogenously.

A successful cure therefore with the therapeutic possibilities available at present is therefore dependent to a large extent upon the therapeutically supplied ceramides being able to penetrate into the skin more rapidly than they are included in the existing physiological decomposition steps and them being supplied continuously over a fairly long period of time, in extreme cases, for life.

The present problem cannot be readily resolved. Certain physiological and physical-chemical or biochemical limits are set upon the rate of absorption of ceramides into the stratum corneum, for example with respect to the diffusion rate of the ceramides. This rate cannot be arbitrarily increased. On the other hand, the ceramide-synthesising and ceramid-metabolising enzymes involved in the mentioned reaction sequences cannot be influenced by exogenous measures or not without serious problems in the sense of increasing (synthesising enzymes) or decreasing their activity (metabolising enzymes).

The first-mentioned therapeutic approach, i.e. the activation of lipid-synthesising enzymes by exogenous active substances (e.g. nicotineamide) is possible only to a limited extent and to date has only succeeded in vitro (Tanno O, Ota Y, Kitamura N, Katsube T, Inoue S (2000): British J. Dermatol, 143(3): 524-531). The second therapeutic approach, i.e. the inhibition of lipid-metabolising enzymes by exogenous active substances has obviously to date not yet been successful since obviously inhibitors of lipid-metabolising enzymes with sufficiently high specificity do not exist.

In order to resolve the described problem it is necessary basically to apply other principles in order to increase the therapeutic efficacy of exogenously supplied lipid substitute substances or analogue substances.

The object of the present invention is therefore to provide compounds by means of which the biological membranes present in the organism can be stabilised, the water-binding capacity of the various skin layers can be increased and the transepidermal water loss (TEWL) of the skin can be reduced.

There should be understood by stabilisation of the biological membrane in the present case, the process that the active substances according to the invention, after incorporation in the biological membrane, display a lower tendency, relative to the ceramides known from prior art, to leave the membrane, i.e. have greater sustainability of their cosmetic and clinical efficacy.

This object is achieved by the features of the ceramide dimers described herein, with respect to use as pharmaceutical preparation and, with respect to use as cosmetic preparation, and the advantageous developments thereof.

According to the invention, ceramide dimers are provided which are constructed from two ceramide molecules which are crosslinked to each other via their lipophilic end.

It is thereby irrelevant whether the binding is effected via the alkyl group of the sphingosine basic body or via the fatty acid radical or via both groups or radicals.

The ceramide dimers thereby have at least one hydrophilic group respectively at the hydrophilic end for increasing the hydration shell of the dimer.

The compounds according to the invention from the group of ceramide dimers have the following properties:

The basic structure of the ceramides used, which enables formation of a lipid double membrane, is not only maintained but the capacity for forming the double membrane is increased because the skin damaged by the mentioned diseases has in any case merely a restricted capacity for constructing and maintaining the physiological lipid double membrane.

The structure of the ceramides used is changed, whilst the basic structure is maintained, such that they can still only function to a lesser extent than substrates of the metabolising enzymes present in the skin, in particular in the stratum corneum. This means that they are included to a significantly lesser extent than the original ceramides in the respective enzymatic reaction sequences and hence they are maintained as essential structural components of the stratum corneum over a longer period of time than the original ceramides.

The modification of the special ceramide molecular structure is however effected, on the other hand, only to such a small extent that, due to the low metabolism-caused conversion or decomposition of the supplied ceramides, those substances are produced which are as similar as possible to the naturally occurring body ceramides. In this way, the danger that metabolism products with a toxic effect are produced is significantly reduced.

A comparatively small, controllable decomposability of the ceramide dimers is achieved by the covalent bond between the two original ceramide molecules being effected via an oxygen atom. This oxygen atom acts as metabolic predetermined breaking point since e.g. mixed functional monooxygenases attack oxidatively the carbon atoms present in the immediate vicinity of the oxygen atom, which leads to disintegration of the ceramide dimer with formation of the co-hydroxylated or carboxylated original ceramides.

By bonding of a further molecule with pronounced hydrophilic properties to the hydrophilic molecule part of the ceramides, the hydration shell of the ceramide dimers is increased, which leads consequently to an increase in the water-binding capacity of the relevant skin layers and to a reduction in the transepidermal water loss (TEWL).

These properties are thereby produced according to the invention in the following way:

By coupling two ceramide molecules to form ceramide dimers, it is ensured that such a molecule is decomposed or converted very much more slowly by the enzymes of the ceramide metabolism present in the organism than applies to the original ceramides. The molecule enlargement associated with the covalent bond between two ceramide molecules leads to a great reduction in the enzymatically-controlled metabolisation because, with the known high substrate specificity of most enzymes, the (approximate) doubling in size of the ceramide molecule allows the rate of the ceramide conversion or ceramide decomposition to be significantly reduced.

On the other hand, the resulting decomposition products are so similar in their general construction to the naturally occurring resulting products of the ceramide metabolism that inclusion in the corresponding reaction sequences is possible after a slowly proceeding decomposition of the active substances according to the invention without problems. Furthermore, it need not be taken into account in any manner that the ceramide dimers have relevant toxicity because of the high similarity to the original ceramides.

A certain degree of enzymatic metabolisation of the ceramide dimers, which can be regarded however as significantly less than that of the monomeric ceramides, is hence a property of the active substances which is desired for pharmacokinetic and pharmacodynamic reasons because, as a result, the controllability of the therapy is better ensured than if no metabolic decomposition were possible.

A certain controlled metabolisation rate of the ceramide dimers can be achieved by an oxygen atom being present between the two coupled ceramides. The carbon atoms in the vicinity of this oxygen atom can be hydroxylated enzymatically, for instance by the cytochrome-P450-dependent mixed functional monooxygenases. Such a hydroxylation taking place in the immediate vicinity of the oxygen atom leads to the formation of unstable compounds with a semiacetal structure which decompose into the corresponding reaction products. The one reaction product is a ceramide molecule with co-position OH group, the other reaction product is a ceramide molecule with co-position aldehyde function which is further oxidised to form the carboxylic acid group. It is hence obvious that, as a result of an oxidatively proceeding biochemical decomposition of the described ceramide dimers, reaction products are produced which are very similar to the starting compounds of the monomeric ceramides.

A further essential aspect of the pathogenesis of the above-mentioned skin changes or skin diseases is the reduced water-binding capacity of the skin tissue, in particular in the region of the stratum corneum. Physiologically, the water is incorporated not within but, since a plurality of lipid layers disposed in parallel are present, in the space between the individual lipid bilayers. This is due to the fact that the interior of the lipid bilayer is constructed from the strongly hydrophobic fatty acid esters, e.g. the ceramides, whilst the medium outside the lipid bilayer is of a hydrophilic nature. Storage of water in the hydrophobic interior regions of the lipid double membrane is in practice not possible.

The initially mentioned skin changes and diseases can be attributed, on the one hand, to the loss of part of the lipids, in particular of the ceramides, from the lipid bilayers which are disposed in parallel, on the other hand to the partial loss of water from the hydrophilic intermediate layers disposed between these bilayers. The aim of the therapeutic measures in these diseases is hence not only the reconstruction and stabilisation of the lipid bilayers themselves, as is effected with the help of the above-described ceramide dimers, but in addition also the construction and stabilisation of a pronounced hydrosphere on the surface of the lipid bilayer, which are of crucial importance for the water-binding capacity of the skin.

In fact, a certain quantity of water is bonded to the lipid bilayers and hence contributes to the natural water reservoir of the skin. In the case of ageing or diseased skin, this water-binding capacity obviously no longer suffices however to maintain the natural structure of the skin. It is therefore necessary to increase this water-binding capacity of the lipid bilayers by coupling in addition hydrophilic groups to the hydrophilic molecule parts of the ceramide dimers.

It is thereby irrelevant whether the bond is effected via the hydroxyl group or the hydroxymethylene group of the sphingosine basic body.

Hydrophilic groups with an increased tendency for bonding of water are strongly polar compounds, in particular with positive or negative charges and/or with those functional groups which are able to accumulate water via hydrogen bridge bonds. There are included in particular herein amino acids, which have strongly polar groups or charges: —COOH, —$NH_2$, —COO$^-$ and —$NH_3^+$, preferably serine, threonine, lysine, arginine, histidine, aspartic acid, glutamic acid, asparagine, glutamine, tyrosine, and tryptophan, polyols, such as ethane diol or glycerine (propanetriol) with a plurality of —OH groups in the molecule which are enabled to form hydrogen bridge bonds, sugars such as glucose or galactose in which a plurality of OH groups is present in the molecule, sugar derivatives, such as glucuronic acid or galacturonic acid with a plurality of OH groups and a dissociable —COOH group, sugar derivatives, such as amino sugar, which represent components of the strongly water-binding hyaluronic acid, organic acids, such as di- or tricarboxylic acids, malonic acid, succinic acid, malic acid or citric acid, their further carboxyl radicals not used for the bond to the lipid molecule are present dissociated and therefore charged, which accompanies a high water-binding capacity, inorganic acids, such as e.g. sulphate and phosphate which have a very high water-binding capacity due to their charges present in the molecule. Cholesterol sulphate occurs as natural component of biological membranes, choline as physiological substance with a (positively charged) quaternary N-atom, derivatives of urea: this compound (also presented in German with the English title "urea") is, in free form, already a component of many ointments nowadays, with which an increase in water-binding capacity of the skin is intended to be effected.

Preferably the ceramide molecules have the general formulae I to III on the basis of sphingosine, 6-hydroxysphingosine and phytosphingosine:

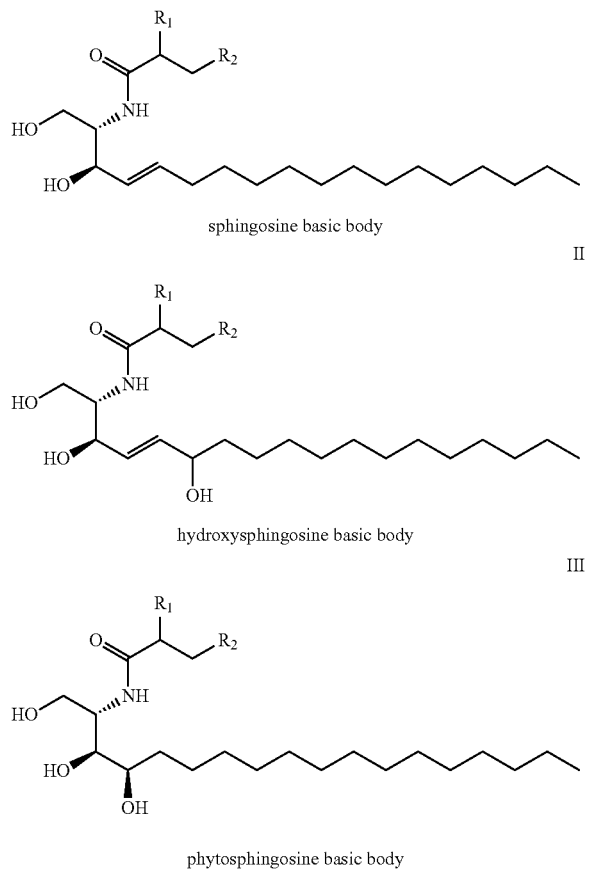

sphingosine basic body hydroxysphingosine basic body phytosphingosine basic body respectively with $R_1$=H or OH and $R_2$=branched or straight-chain $C_1$-$C_{16}$ alkyl radical which can be substituted possibly with heteroatoms or ω-hydroxyalkyl radical esterified with linoleic acid.

The ceramides used for this consist preferably of the compounds described previously in the scientific literature, ceramide 1 (ceramide EOS), ceramide 2 (ceramide NS), ceramide 3 (ceramide NP), ceramide 4 (ceramide EOH), ceramide 5 (ceramide AS), ceramide 6(ceramide AP), ceramide 7 (ceramide AH), ceramide 8(ceramide NH) and ceramide 9 (ceramide EOP) and also the corresponding ω-hydroxyceramides. However, the mentioned ceramides do not represent uniform substances with a precisely defined relative molar mass, rather each ceramide represents a family of compounds with a different length of the amide-like bonded fatty acid present in the molecule and/or the alkyl radical present in the sphingosine component.

The ceramide molecules are preferably connected to each other covalently via their lipophilic end. The ceramide molecules can thereby be connected also via a spacer. The spacer thereby consists preferably of at least one atom selected from the group consisting of carbon, nitrogen or oxygen or combinations hereof, preferably consisting of an oxygen atom or a —O—$(CH_2)_n$—O— group with n=1 to 20. It is likewise possible that the spacer comprises one of the mentioned groups.

According to the invention, the previously described ceramide dimer is likewise provided for use as pharmaceutical preparation.

According to the invention, the ceramide dimer, as was described previously, is provided for producing a pharmaceutical preparation for the treatment of diseases in which a disorder of the lipid composition of the cell membranes of an organism with respect to its content of ceramides and sphingosines is present.

The previously described ceramide dimer can also be used for the production of a pharmaceutical preparation for the treatment of diseases in which a disorder of the composition of the lipid bilayers of the stratum corneum of the skin with respect to its content of ceramides and sphingosines is present.

A further use of the ceramide dimers according to the invention relates to the production of cosmetic preparations, in particular as cream, ointment, lotion, emulsion, gel, spray, cosmetic oil or liposomes.

With reference to the subsequent Figures and examples, the subject according to the invention is intended to be explained in more detail without wishing to restrict said subject to the special embodiments shown here.

Figure 6:
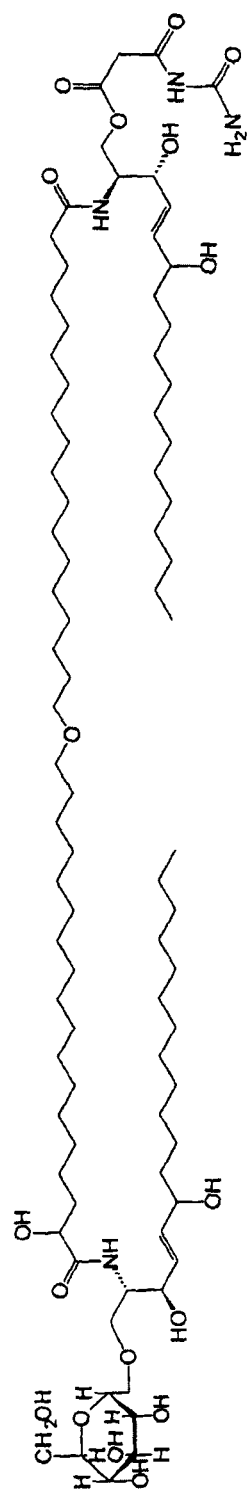

FIG. 6 shows an active substance according to the invention in which the lipid component consists of one molecule ceramide 7 and one molecule ceramide 8. In order to increase the hydrophilia of the hydrophilic molecule areas lying on the membrane surface, a glucose radical is coupled to the ceramide 7 and a urea derivative (comprising a malonic acid radical) is coupled to the ceramide 8.

Figure 7:
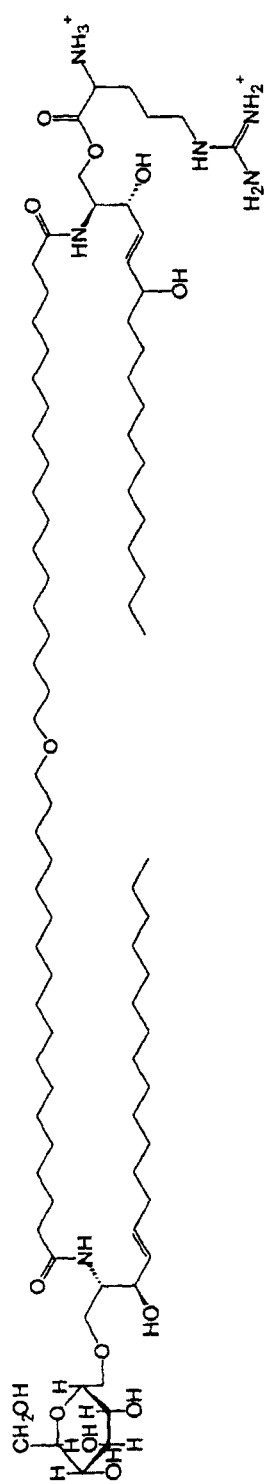

FIG. 7 shows an active substance according to the invention in which the lipid component consists of one molecule ceramide 2 and one molecule ceramide 8. In order to increase the hydrophilia of the hydrophilic molecule areas lying on the membrane surface, a glucose radical is coupled to the ceramide 2 and an arginine radical to the ceramide 8.

EXAMPLE

According to the specialist dermatological report of Dermatest (R) GmbH, 48143 Münster, the active ingredients according to the invention

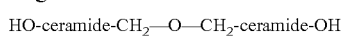

Figure 1:
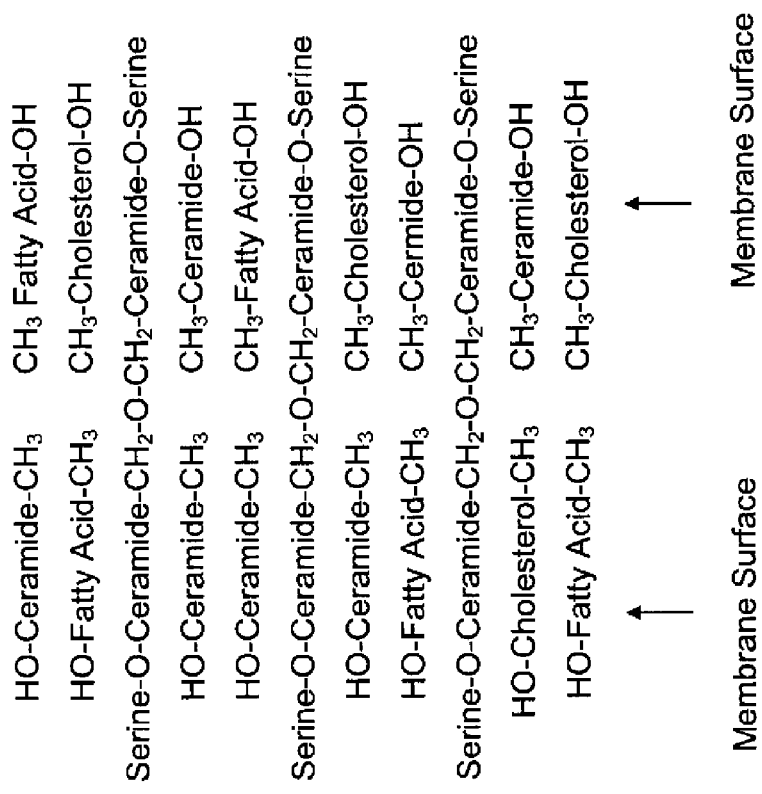
FIG. 1 shows the schematic construction of biological membranes of the stratum corneum from the main lipids, ceramides, cholesterol and free fatty acids with the additional incorporation of ceramide dimers with two coupled serine radicals.
Figure 2:
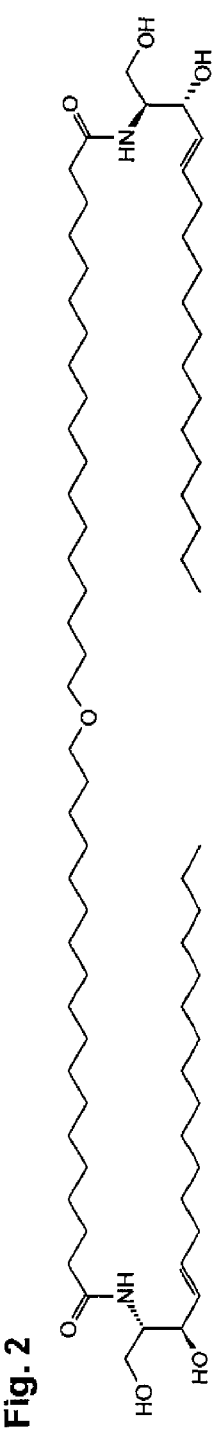
FIG. 2 shows an active substance according to the invention in which the lipid component consists of a dimer of the ceramide 2.
Figure 3:
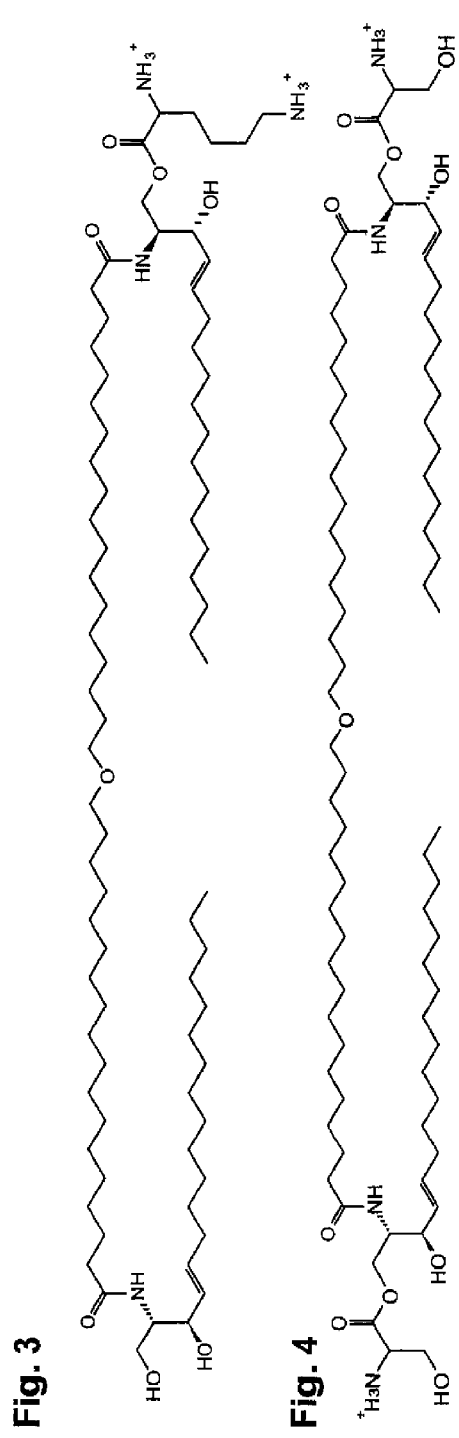
FIG. 3 shows an active substance according to the invention in which the lipid component consists of a dimer of the ceramide 2. In order to increase the hydrophilia of the hydrophilic molecule areas lying on the membrane surface, a lysine radical is coupled to one of the two ceramide-2-components.

("dimer", corresponding to FIG. 2) and

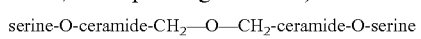

Figure 4:
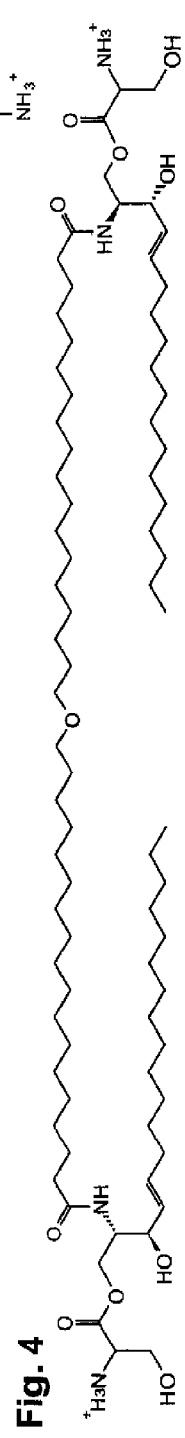
FIG. 4 shows an active substance according to the invention in which the lipid component consists of a dimer of the ceramide 2. In order to increase the hydrophilia of the hydrophilic molecule areas lying on the membrane surface, respectively one serine molecule is coupled to the two ceramide-2-components.
Figure 5:
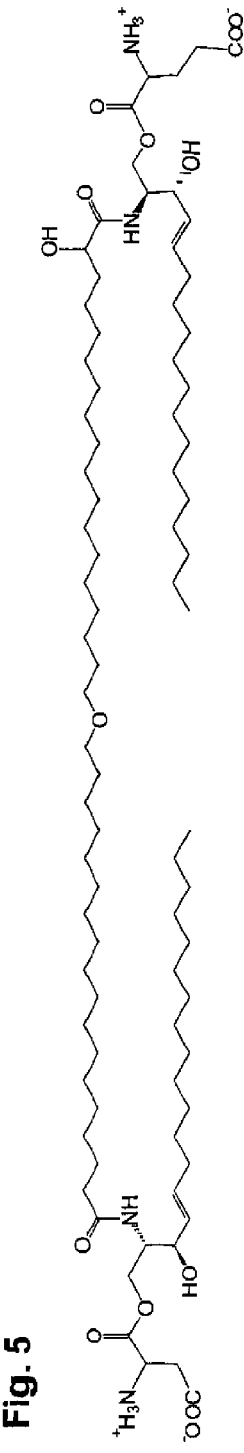
FIG. 5 shows an active substance according to the invention in which the lipid component consists of one molecule ceramide 2 and one molecule ceramide 5. In order to increase the hydrophilia of the hydrophilic molecule areas lying on the membrane surface, a glutamic acid radical and an aspartamic acid radical are coupled to the two ceramide components.

("serine dimer", corresponding to FIG. 4)
with ceramide-2 as ceramide component with respect to the corneometery (water-binding capacity) and TEWL (water loss) in the case of 10 subjects with neurodermitis and 10 subjects with xeroderma after 1, 2 and 4 weeks, show the following results (all data in % change relative to the initial value):

Dimer (Corresponding to FIG. 2):
Corneometry (Water-Binding Capacity):

|  | 1 week | 2 weeks | 4 weeks |
| --- | --- | --- | --- |
| all 20 subjects | +24.05 | +28.02 | +37.60 |
| 10 subjects neurodermitis | +25.63 | +28.62 | +43.40 |
| 10 subjects xeroderma | +22.52 | +27.42 | +31.90 |

TEWL (Water Loss):

|  | 1 week | 2 weeks | 4 weeks |
| --- | --- | --- | --- |
| all 20 subjects | −8.65 | −13.32 | −16.75 |
| 10 subjects neurodermitis | −7.81 | −13.50 | −17.02 |
| 10 subjects xeroderma | −9.46 | −13.04 | −16.39 |

In the case of the TEWL value, the reduction in water loss is detected. This means that that the effectiveness of the active substance according to the invention is all the higher, the more negative the measuring value.

Serine Dimer (See FIG. 4):
Corneometry (Water-Binding Capacity):

|  | 1 week | 2 weeks | 4 weeks |
| --- | --- | --- | --- |
| all 20 subjects | +25.43 | +29.49 | +40.87 |
| 10 subjects neurodermitis | +27.71 | +32.88 | +47.43 |
| 10 subjects xeroderma | +23.23 | +26.21 | +34.53 |

TEWL (Water Loss):

|  | 1 week | 2 weeks | 4 weeks |
| --- | --- | --- | --- |
| all 20 subjects | −7.80 | −12.57 | −15.37 |
| 10 subjects neurodermitis | −6.20 | −9.74 | −12.84 |
| 10 subjects xeroderma | −9.36 | −15.45 | −17.93 |

The results of the implemented dermatological tests imply that both active substances according to the invention have good to very good effectiveness with respect to the (desired) increase in water-binding capacity of the skin and with respect to the (desired) reduction in water loss from the skin.

A differentiated evaluation of the results shows that the serine dimer has a more favourable effect on the water-binding capacity of skin than the dimer. This effect occurs in particular in the presence of neurodermitis.

On the other hand, the dimer has a somewhat more favourable effect on the water loss from the skin than the serine dimer in the case of neurodermitis.

The invention claimed is:

1. A ceramide dimer comprising two ceramide molecules, wherein the ceramides have a sphingosine basic body, hydroxysphingosine basic body or a phytosphingosine basic body according to one of the general formulae I to III:

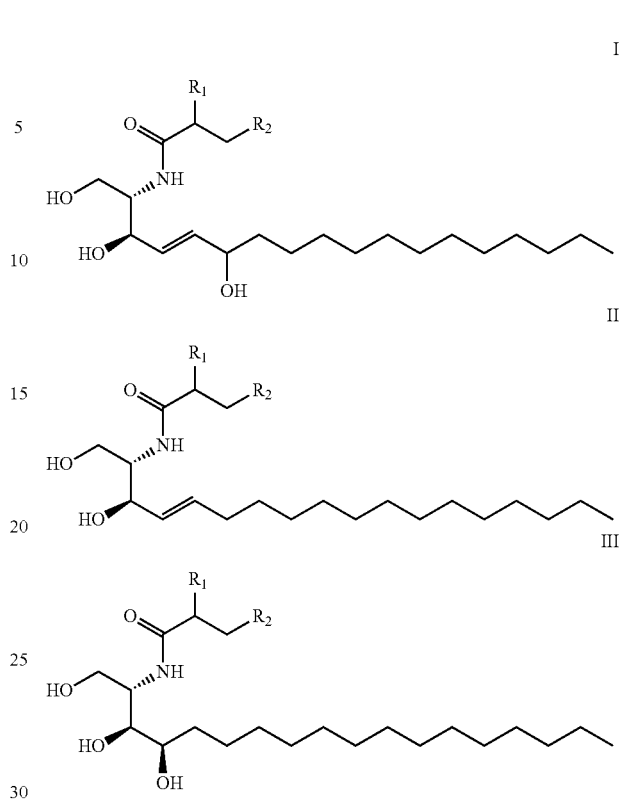

respectively with
$R_1$=H or OH and
$R_2$=branched or straight-chain $C_1$-$C_{16}$ alkyl radical which is substituted with heteroatoms or unsubsituted, or
$R_2$=ω-hydroxyalkyl radical esterified with linoleic acid,
wherein the ceramide molecules are bonded covalently to each other via a spacer at their lipophilic end, either via the alkyl chain of the sphingosine basic structure or via the fatty acid radical or via the combination of both attack points, wherein the spacer consists of an oxygen atom or an —O—$(CH_2)_n$—O— group with n=1 to 20, wherein at the hydrophilic end of the ceramide molecules, via the hydroxyl group or the hydroxymethylene group of the sphingosine basic body, at least one hydrophilic group is disposed for increasing the hydration shell of the dimer, wherein the hydrophilic group is selected from the group consisting of amino acids, polyols, sugars, organic acids, inorganic acids, choline, urea, and also combinations thereof.

2. The ceramide dimer according to claim 1, wherein the hydrophilic group is selected from the group consisting of
amino acids with polar groups or charges,
ethane diol or glycerine,
glucose or galactose, sugar derivatives with a dissociable —COOH group,
di- or tricarboxylic acids,
sulphuric or phosphoric acids,
and also combinations thereof.

3. The ceramide dimer according to claim 1,
wherein the ceramide molecules are selected from the group consisting of ceramide 1, ceramide 2, ceramide 3, ceramide 4, ceramide 5, ceramide 6, ceramide 7, ceramide 8, ceramide 9 and also ω-hydroxyceramides thereof.

4. A pharmaceutical preparation comprising the ceramide dimer according to claim 1.

5. A method for treating diseases, wherein the disease includes a disorder of the composition of the lipid bilayers of the stratum corneum of the skin with respect to its content of ceramides, ω-hydroxyceramides and sphingosines, comprising administering the dimer according to claim 1.

6. A cosmetic preparation comprising the ceramide dimer according to claim 1.

7. The cosmetic preparation of claim 6, wherein the cosmetic preparation is a cream, ointment, lotion, emulsion, gel, spray, cosmetic oil or liposomes.

8. A method for treating diseases, wherein the disease includes a disorder of the lipid composition of the cell membranes of an organism with respect to its content of ceramides, ω-hydroxyceramides and sphingosines, comprising administering the dimer according to claim 1.

* * * * *